United States Patent [19]
Iacobucci

[11] Patent Number: 5,202,235
[45] Date of Patent: * Apr. 13, 1993

[54] ENZYMATIC METHOD FOR THE SYNTHESIS AND SEPARATION OF PEPTIDES

[75] Inventor: Guillermo A. Iacobucci, Atlanta, Ga.

[73] Assignee: The Coca-Cola Company, Atlanta, Ga.

[*] Notice: The portion of the term of this patent subsequent to Mar. 26, 2008 has been disclaimed.

[21] Appl. No.: 635,941

[22] Filed: Dec. 28, 1990

Related U.S. Application Data

[62] Division of Ser. No. 897,679, Aug. 18, 1986, Pat. No. 5,037,741.

[51] Int. Cl.$^5$ .................... C12P 21/02; C12N 11/18; C12M 1/00
[52] U.S. Cl. .................... 435/68.1; 435/70.1; 435/175; 435/288
[58] Field of Search ............ 210/632, 638; 435/68.1, 435/803, 70.1, 813, 71.1, 819, 280, 174, 288, 284, 41, 175, 286, 182, 285; 422/149, 236, 238; 530/344, 801; 560/38, 40, 41

[56] References Cited

U.S. PATENT DOCUMENTS

| | | | |
|---|---|---|---|
| 3,625,734 | 12/1971 | Ward, III | 117/46 |
| 3,779,907 | 12/1973 | Li et al. | 210/22 |
| 3,813,317 | 5/1974 | Benoiton et al. | 435/280 |
| 3,933,781 | 1/1976 | Bachman | 260/112.5 |
| 4,119,408 | 10/1978 | Matson | 422/177 |
| 4,119,493 | 10/1978 | Isowa | 435/68.1 |
| 4,187,086 | 2/1980 | Walmet et al. | 55/16 |
| 4,215,631 | 2/1981 | Simon | 435/106 |
| 4,455,210 | 9/1984 | Coker et al. | 204/283 |
| 4,622,417 | 11/1987 | Barnett et al. | 530/801 |
| 4,670,151 | 6/1987 | Bitter | 210/648 |
| 4,743,547 | 5/1988 | Kiramura et al. | 435/108 |
| 4,786,597 | 11/1988 | Matson et al. | 435/41 |
| 4,921,612 | 5/1990 | Sirkar | 435/41 |
| 4,956,289 | 9/1990 | Wrasidlo et al. | 435/182 |
| 5,002,871 | 3/1991 | Iaccohucci | 435/68.1 |

FOREIGN PATENT DOCUMENTS

| | | |
|---|---|---|
| 0017485 | 10/1980 | European Pat. Off. . |
| 75160 | 3/1983 | European Pat. Off. . |
| 0121265 | 10/1984 | European Pat. Off. . |
| 0124313 | 11/1984 | European Pat. Off. . |
| 0149594 | 7/1985 | European Pat. Off. . |
| 0188342 | 7/1986 | European Pat. Off. . |
| 902474 | 5/1985 | France . |
| 2047564A | 3/1979 | United Kingdom . |

OTHER PUBLICATIONS

Liquid-Membrane Hollow Fiber Enyme Reactors, Enzyme Engineering vol. 3, pp. 19–28 (1978) Lo. et al.
Two Phase Biocatalytic Reaction, J. Chem. Tech. Biotechnol, vol. 32, 162–169, (1989), Lilly.
"Immobilized Lactose For Whey Hydrolysis Stability And Operating Strategy" Enzyme Engineering vol. 4, pp. 67–76, Brower et al., ed., (1978).
Chem. Abstracts vol. 47, 8015 (1953) Rabinovich, et al.

(List continued on next page.)

Primary Examiner—Richard I. Raymond
Assistant Examiner—Shailendra Kumar
Attorney, Agent, or Firm—Kenyon & Kenyon

[57] ABSTRACT

The present invention provides a method for the enzymatic synthesis of peptides accomplished by shifting the chemical equilibrium that exists in a reaction mixture between charged or ionized reacting amino acids and uncharged or non-ionized peptide product in the presence of a proteolytic enzyme such as thermolysin. The equilibrium is shifted by diffusion of the uncharged peptide product across an ion-rejection membrane which removes the uncharged peptide from the reaction mixture and preferably the diffused uncharged peptide is quickly converted to a charged species that cannot back-diffuse into the reaction mixture so that the uncharged peptide is effectively "pulled" across the membrane.

13 Claims, 4 Drawing Sheets

OTHER PUBLICATIONS

J. Biol. Chem. 1986, 221 (1970) Arvid, et al.
Can. J. Biochem 48, 1058–1065 (1970) Purdie, et al.
Use of N-Formyl Protected Amino Acid Esters In Enzyme-Catalyzed Peptide Synthesis, Chemical Abstracts, vol. 113, 593–596, (1990) Floersheimer.
Continuous Synthesis On N-(Benzyloxycarbonyl-)-L-Aspartyl L-Phenylalanine Methyl, Ester With Inmobilized Thermolysis In An Organic Solvent Biotechnology vol. 3, 459–464, (May, 1985).
Kagaku Sosethsu 35, 195 (1982 (Toyo Soda).
Enzyme Engineering, 7 vol. 434, pp. 95–98 (Oyama), 1985.
Coupling Separation And Enrichment To Chemical Conversion In A Membrane Reactor, Aicle Annual Meeting Nov. 8–12, 1981 (Matson, et al.).
Peptide Synthetic Chemistry pp. 53 to 59 Willi & Koleman, 1987.
Membrane Reactors In Bioprocessing (Matson), 152–165, Annal. N.Y. Acad. Sci 469, 1986.
Synthesis Of An Aspartame Precursor By Immobilized Thermolysin In An Organic Solvent, Journal of Organic Chemistry vol. 46, 5241–5242 (1981).

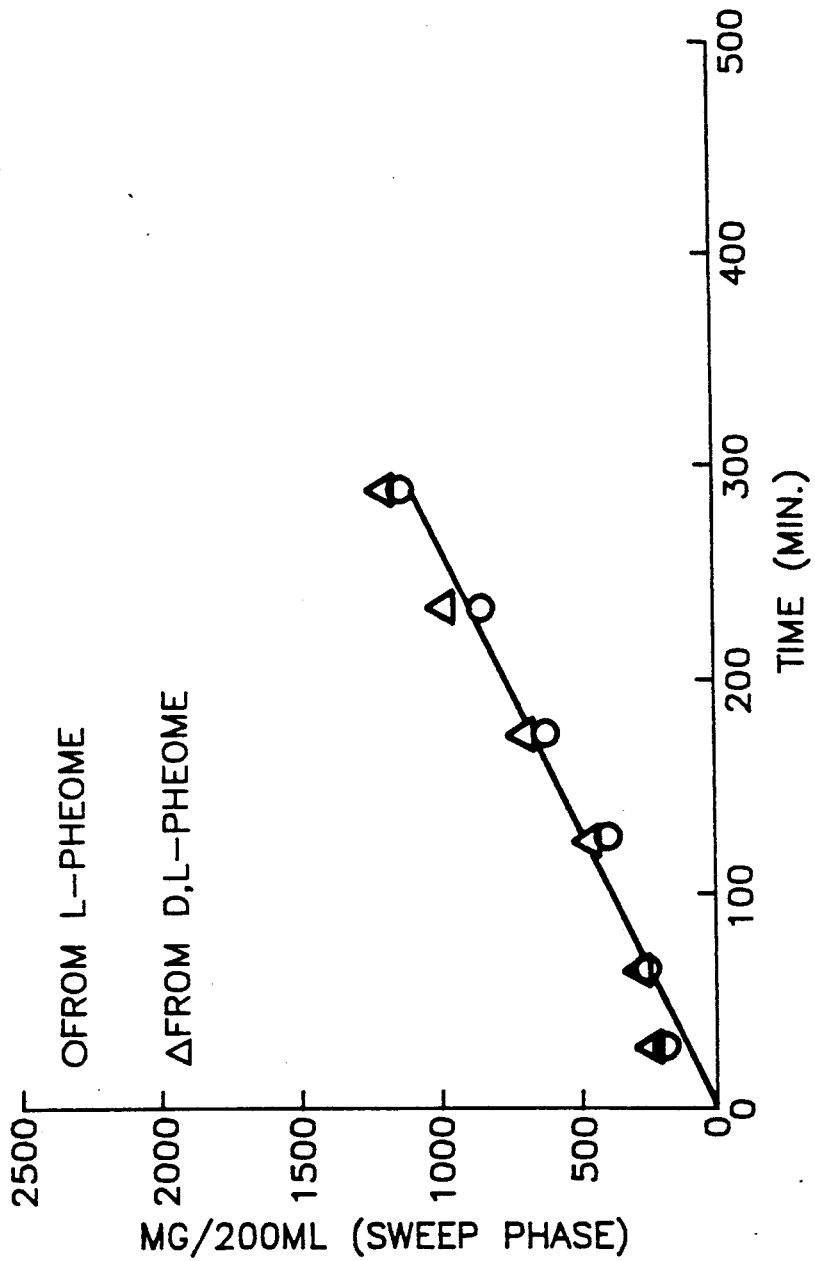

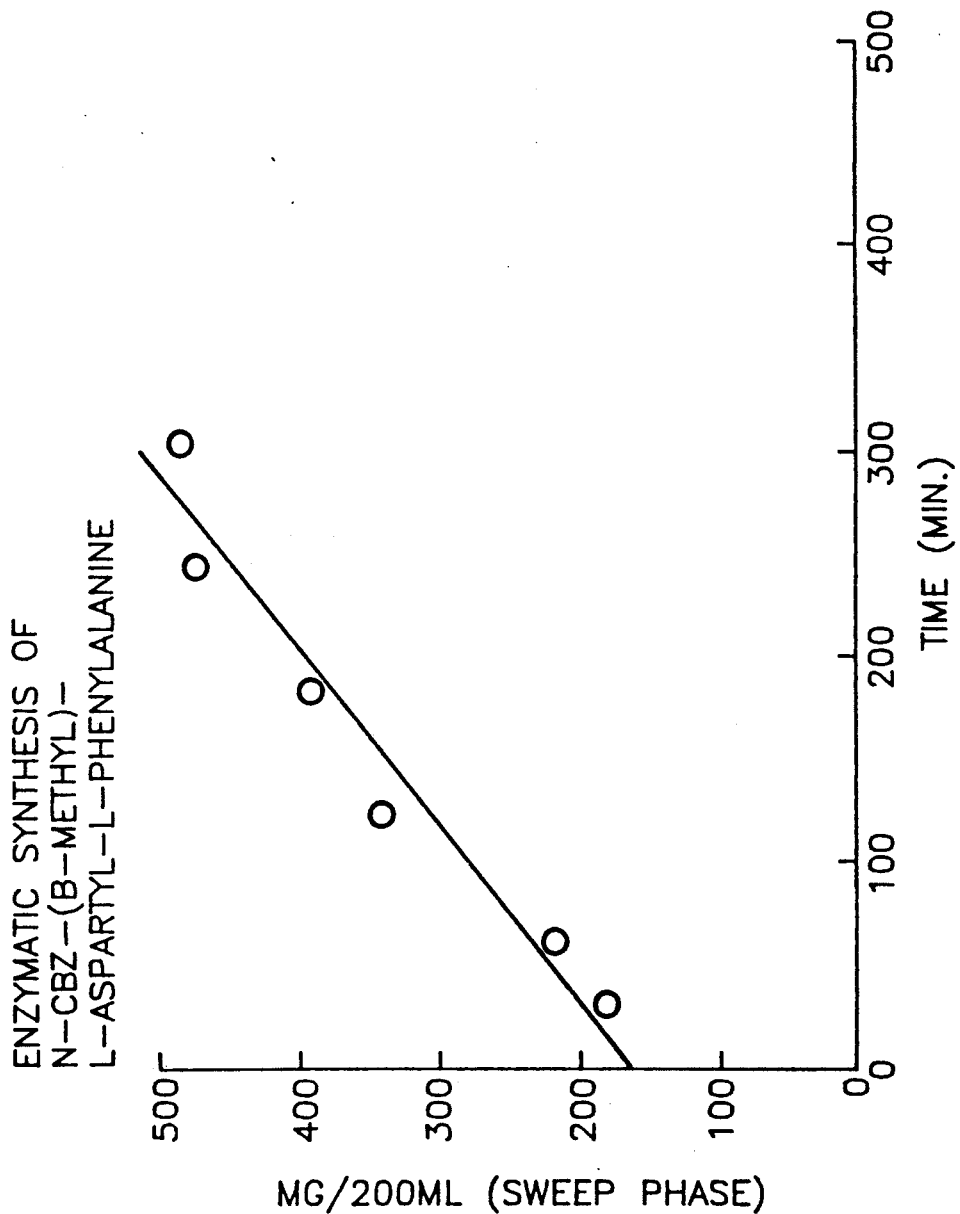

ENZYMATIC METHOD FOR THE SYNTHESIS AND SEPARATION OF PEPTIDES

This application is a continuation, of application Ser. No. 06/897,679, filed Aug. 18, 1986, now U.S. Pat. No. 5,037,741.

FIELD OF THE INVENTION

The present invention relates generally to an enzymatic method for the synthesis and separation of peptides employing a membrane permeable to uncharged peptides but impermeable to charged molecules; and, more particularly, to the simultaneous synthesis and purification of L,L-dipeptides, and its application to the preparation of L-aspartyl-L-phenylalanine methyl ester (aspartame).

BACKGROUND OF THE INVENTION

The use of proteolytic enzymes as condensation catalysts for the stereospecific coupling of two L-amino acids to yield L, L-peptides is known since the early days of protein chemistry. As early as 1909 Mohr and Strohschein described the formation of the water-insoluble dipeptide Bz-Leu-Leu-NH$_2$ by reacting Bz-Leu-OH and H-Leu-NH$_2$ in the presence of the protein degrading enzyme papain. E. Mohr and F. Strohschein, Ber 42, 2521 (1909). The Mohr and Strohschein-type reaction is possible only between those amino acids that form peptide bonds that are susceptible to cleavage by the papain or other enzyme used. Indeed, the condensing reaction's equilibrium between the amino acid reactants and peptide product is largely displaced towards the reacting amino acids. Nevertheless, the condensing reactant can be driven to completion by mass action if, e.g., the dipeptide product is poorly soluble and precipitates out of the reaction phase.

Due to the commercial importance of certain peptides and the fact that enzymes are known to catalyze peptide formation under mild conditions there has been a great deal of research done on the enzymatic synthesis of peptides particularly simple dipeptides. K. Oyama and K. Kihara, *Kagaku Sosetsu* 35, 195 (1982); K. Oyama and K. Kihara, *ChemTech.* 14, 100 (1984).

The process for enzymatic synthesis of the peptide derivative aspartame, described in U.S. Pat. No. 4,165,311, hereinafter the '311 process, involves the thermolysin-catalyzed condensation of N-carbobenzoxy-L-aspartic acid with D,L-phenylalanine methyl ester and precipitation of an intermediary complex, D-phenylalanine methyl ester salt of N-carbobenzoxy-aspartame, to drive the reaction to the peptide product side. Further processing of this intermediary complex allows for the recovery of D-phenylalanine methyl ester, that may be recycled after racemization, and of the N-carbobenzoxy-aspartame derivative which can be converted to aspartame by elimination of the N-carbobenzoxy protecting group. The '311 process must be practiced on a batch basis which is cumbersome and complicates the recovery of enzyme. Also see: K. Oyama, S. Irino, T. Harada and N. Hagi, *Ann. N.Y. Acad. Sci.* 434, 95 (1985).

The N-carbobenzoxy protecting group plays an essential role in the '311 process by: fulfilling the structural requirement imposed by the active site of thermolysin; and by contributing to the insolubility of the intermediary complex thereby increasing the yield of the reaction. Elimination of the N-carbobenzoxy protecting group from the aspartame derivative must be effected under mild conditions, e.g., catalytic hydrogenation, to prevent cleavage of the methyl ester function. Catalytic hydrogenation involves the inconvenience of handling hydrogen gas on a large scale.

Alternative approaches to driving enzymatic condensation reactions to completion have also been described in the chemical literature. For example, the use of organic solvents as reaction media has been found effective for increasing the peptide product yields; although, the concomittant decrease in enzyme stability has precluded its practice on a large scale. K. Oyama, S. Nishimura, Y. Nonaka, K. Kihara and T. Hashimoto, *J. Org. Chem.* 46, 5241 (1981); H. Ooshima, H. Mori and Y. Harano, *Biotechnology Letters* 7, 789 (1985); K. Nakanishi, T. Kamikubo and R. Matsuno, *Biotechnology* 3, 459 (1985).

In view of the above-noted difficulties in the practice of prior art methods for enzymatic synthesis of peptides, particularly, the requirements for precipitation of an intermediary complex and handling of dangerous reagents; it would be desirable to provide an improved process that avoids these difficulties and that safely provides effective yields without rapid deactivation of the enzyme catalysts.

SUMMARY AND OBJECTS OF THE INVENTION

It is an object of the present invention to provide a process for the enzymatic synthesis of peptides which provides for simultaneous synthesis and purification of the peptide product.

It is another object of the present invention to provide a process for the safe, economical and efficient synthesis and purification of peptides and derivatives thereof, particularly aspartame.

It is another object of the present invention to provide an economical process for the enzymatic synthesis of peptides that provides for the efficient use of enzyme and the means to effect the synthesis on a continuous basis.

It is yet another object of the present invention to provide a process particularly adapted to the enzymatic synthesis of aspartame and its derivatives with D, L-phenylalanine and N- protected-$\beta$-substituted-L-aspartate in substantially quantitative yield.

The present invention provides a method for the synthesis and purification of a compound, comprising the steps of coupling a first reactant with a second reactant to produce a membrane transportable compound; transporting the transportable compound across a membrane that will not transport the reactants; and irreversibly converting the transported compound to a form that cannot be transported across the membrane.

The present invention also provides a process for the enzymatic synthesis and purification of compounds comprising the steps of coupling a first compound, including a protonated amino group (ammonium), and a second compound, including a free carboxylate group, using a condensation enzyme in an aqueous mixture to produce an uncharged coupled compound; continuously removing the uncharged coupled compound from the aqueous mixture by diffusion across a membrane that selectively transports the uncharged coupled compound to the product side of the membrane. Preferably, the transported coupled compound is a peptide or derivative thereof that is converted to a charged molecule so that it does not back-diffuse across the membrane.

Thus the formation of the coupled compound product is favored in the reaction mixture because it is constantly being removed therefrom.

The present invention also provides a process for the enzymatic synthesis of peptide derivatives, such as aspartame and their analogs, comprising the steps of condensing a N-acyl-$\beta$-substituted-L-aspartic acid including an $\alpha$-carboxylate group with a phenylalanine lower alkyl ester including an $\alpha$-ammonium group in an aqueous reaction mixture including a condensation enzyme, to form N-formyl-L-aspartyl ($\beta$-substituted)-L-phenylalanine lower alkyl ester (i.e. 1–6 carbons), an uncharged peptide; and transporting the uncharged peptide from the aqueous reaction mixture to a product mixture across a permselective membrane.

The present invention also provides a method for the enzymatic synthesis of peptides comprising the steps of condensing first and second amino acid compounds in an aqueous initial reaction mixture to form an uncharged compound; transporting the uncharged compound into an aqueous second reaction mixture across a membrane that will not transport substantial amounts of the amino acid compounds; and converting the transported uncharged compound to a form that cannot be retransported across the membrane to the initial reaction mixture.

BRIEF DESCRIPTION OF THE DRAWINGS

The foregoing and other objects and advantages are attained by the invention, as will be apparent from the following detailed description taken in conjunction with the accompanying drawings, wherein:

FIG. 3 is a graph illustrating the quantity of product (aspartame derivative) formed over time in Examples 1 and 2.

FIG. 4 is a graph illustrating the quantity of product (aspartame derivative) formed over time in Example 4.

DETAILED DESCRIPTION OF THE INVENTION

Figure 1:
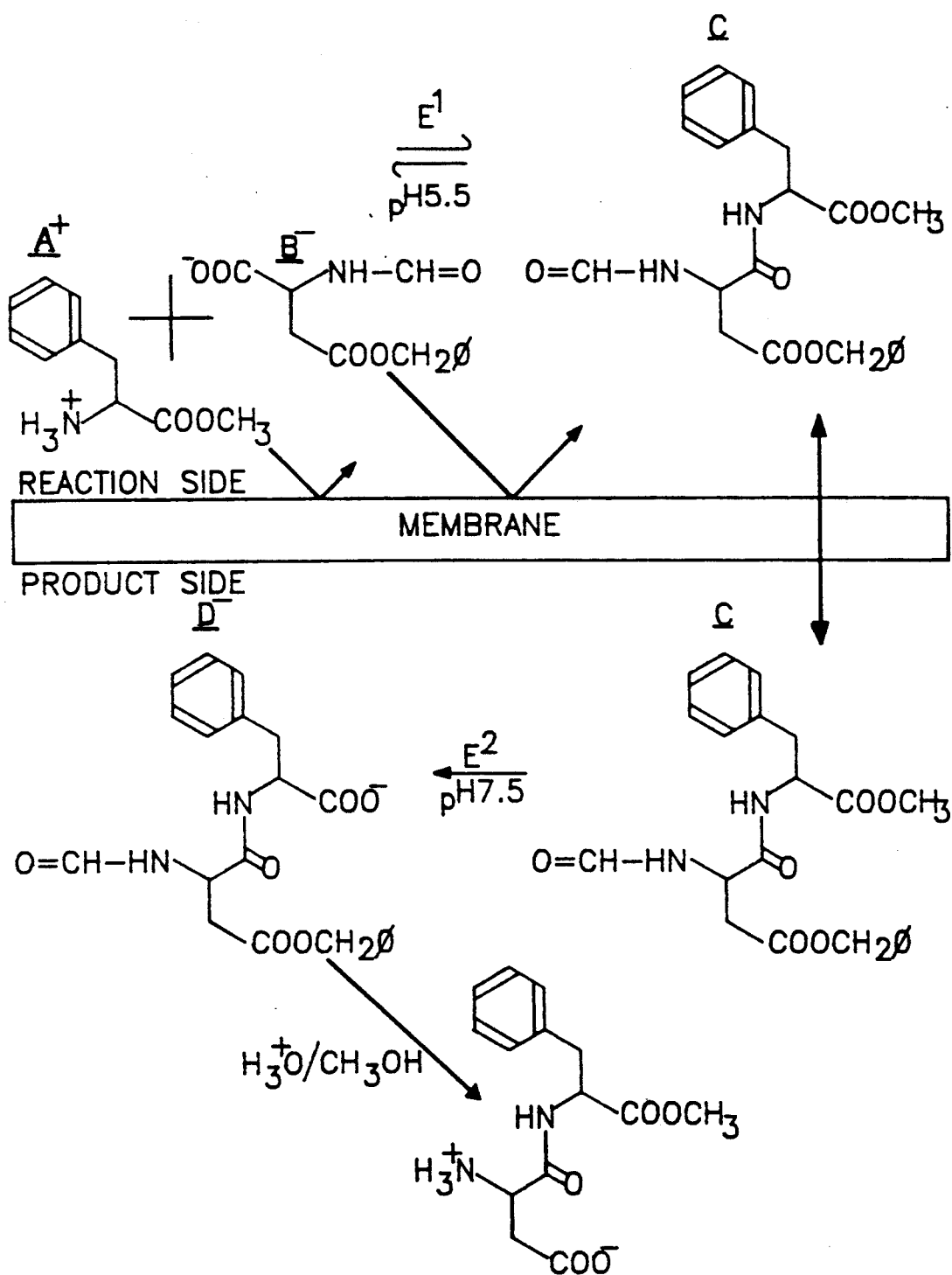
FIG. 1 is schematic illustration of the enzymatic synthesis of aspartame in accordance with the present invention.

The invention disclosed herein provides a procedure for driving to completion the enzymatic synthesis of peptides in an aqueous reaction mixture by separating the uncharged peptide intermediate, or derivative thereof, from the reaction mixture by means of a membrane that selectively transports the uncharged peptide out of the reaction mixture into a product mixture. Because the membrane is substantially impermeable to the reactants (charged molecules) removal of the peptide intermediate from the reaction mixture causes a decrease of peptide concentration at equilibrium that pushes the reaction to completion by mass action.

The membranes most useful in the practice of the present invention are Immobilized Liquid Membranes (ILM) comprising a nonpolar liquid embedded in microporous support material preferably a polymeric sheet that is substantially impervious to the enzymes, reactants and products. Hydrophobic polymers such as polypropylene are preferred support materials; and another polymer for fabricating the microporous support material is TEFLON, a trademark of E. I. DuPont de Nemours & Co. for fluorinated hydrocarbon polymers. A typical microporous support is GORE-TEX, a trademark of W. C. Gore & Associates, Inc.

The micropores pass through the support material and should be sized so that an immobilized liquid will be held therein by capillarity and will not escape therefrom when subjected to, e.g., pressure differentials across the membrane or other ordinary reaction conditions. Subject to the foregoing limitations is advantageous to maximize the contact area between the immobilized liquid and reaction mixture to maximize the rate of transfer (flux) of the uncharged peptide product across the membrane. It will be appreciated that the preferred pore size will vary depending on the properties of the particular immobilized liquid, reactants employed, products produced, and like factors; and further, that the optimum pore size can be determined empirically by those skilled in the art. A useful discussion of pore size selection is found in U.S. Pat. No. 4,174,374 the text of which is incorporated herein by reference. The use and preparation of immobilized liquid membranes are described in the following references, the texts of which are also incorporated herein by reference, S. L. Matson, J. A. Quinn, *Coupling Separation and Enrichment to Chemical Conversion in a Membrane Reactor*, paper presented at the AICHE Annual Meeting, New Orleans, La. Nov. 8–12, 1981) and S. L. Matson and J. A. Quinn, *Membrane Reactors in Bioprocessing*, Ann. N.Y. Acad. Sci. 469, 152 (1986).

The immobilized liquid held in the microporous support by capillarity should be water immiscible and a good solvent for the uncharged peptide product which must be transported across the membrane (diffused) at a reasonable rate, i.e., good transport characteristics/high flux; while, charged or ionized molecules on both the reaction side and product side of the membrane are, for the most part, not transported across the membrane in either direction, i.e., good selectivity/ion rejection.

Selection of the best combination of support material and immobilized liquid for use in an enzymatic synthesis of a peptide in accordance with the present invention will depend, in part, on the nature of the particular reactants employed, products desired and solvents in the system.

The generally preferred immobilized liquids for the practice of the present invention include water-immiscible organic solvents, such as alcohols of 6 to 20 carbons, branched and unbranched, for example, n-decanol, n-dodecanol, n-hexadecanol and mixtures thereof.

Another type of membrane useful in the practice of the invention comprises hydrophobic solid films made of organic polymers like polyvinyl chloride. The preparation of these polymer membranes is well described in the literature, for example, O. J. Sweeting, Editor, *Science and Technology of Polymer Films*, Interscience, New York (1968), while extensive application of such membranes to the separation of gases and liquids are discussed in S. T. Hwang and K. Kammermeyer, *Membranes in Separations, Techniques of Chemistry*, Vol. VII, (A. Weissberger, editor) John Wiley & Sons, Inc., New York (1975).

A preferred embodiment of the invention employs a membrane reactor/separator system which provides an aqueous reaction mixture or phase circulating in contact with one side of an ILM membrane and a product aqueous phase or mixture circulating countercurrently at the opposite surface of the membrane. S. L. Matson and J. A. Quinn, *Ann. N.Y. Acad. Sci.* 469, 152 (1986). The pH and temperature of the reaction and product phases are maintained at a value that keeps the reactants in a form that minimizes their transport across the membrane at pH's between about 4.0 and 8.0 and more preferably between about 4.0 and 6.0. Transport of the uncharged peptide intermediate from the reaction phase to the product phase is driven by the concentration gradient across the membrane created by increasing neutral or uncharged peptide concentration in the reaction phase. The transport activity or flux across the membrane can be significantly enhanced by the simultaneous, irreversible conversion of the transported peptide, in the product phase, to a species that cannot back-diffuse. For example, the latter conversion may result in the formation of a polar peptide that cannot back-diffuse and thus supplement the driving force to achieve completion of the coupling reaction. An example of a membrane reactor/separator that could be adapted for the practice of the present invention is found in U.S. Pat. No. 4,187,086.

Available alternative membrane reactor/separator configurations that could be adapted to practice of the present invention include the hollow fiber modules described in U.K. Patent Application 2,047,564 A, and conventional plate and frame-type filter devices well known in the art.

In addition to selective transport of the uncharged peptide the membrane provides a barrier between the reaction phase and product phase that prevents undesirable mixing of, and reactions between, the components of each phase.

In a preferred membrane reactor/separator configured in accordance with the present invention the chemical equilibrium between the reactants is actually "pulled" across the membrane by conducting an irreversible conversion of the transported uncharged peptide, to a membrane impermeable species, on the product side of the membrane. This type of membrane reactor/separator employs a coupled two enzyme ($E^1$ and $E^2$) process of the general type:

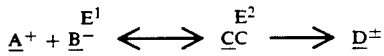

The charged reactants $\underline{A}$ and $\underline{B}$ are amino acids and/or small peptides which are condensed with the aid of peptide forming enzyme $E^1$ to form the uncharged intermediary peptide $\underline{C}$ which is selectively transported across the membrane to the product side. It is understood that reactive functional groups in the reactants that do not participate in the desired reaction may be protected or blocked, where necessary, to prevent undesirable side reactions and/or changes in the products. On the product side of the membrane uncharged peptide $\underline{C}$ is converted to charged peptide $\underline{D}$ which cannot back-diffuse across the membrane, causing the chemical equilibrium in the reaction mixture to shift toward the production of more $\underline{C}$.

This concept is illustrated in FIG. 1, for the specific case of the enzymatic condensation of D,L-phenylalanine methyl ester with (N- and β-protected) N-formyl-β-benzyl-L-aspartate, in the presence of thermolysin at about pH 5.5.

In the reaction scheme illustrated in FIG. 1 the reactant $\underline{A}^+$ is D, L-phenylalanine methyl ester and $\underline{B}^-$ is N-formyl-β-benzyl-L-aspartate. The reactants are condensed on the reaction side of the membrane by the enzyme $E^1$ thermolysin forming the uncharged peptide $\underline{C}$. The pH is selected to maintain the reactants in their charged state and thus minimize their diffusion across the membrane along with uncharged peptide $\underline{C}$.

Although the chemical equilibrium for the condensation reaction largely favors the reactant $\underline{A}^+$ and $\underline{B}^-$ species, diffusion of the uncharged peptide product $\underline{C}$ across the membrane to the product side requires the constant production of $\underline{C}$ to maintain the chemical equilibrium on the reaction side of the membrane.

On the product side on the membrane an esterase enzyme $E^2$ quickly and irreversibly converts the uncharged peptide $\underline{C}$ diffused across the membrane to charged peptide $\underline{D}$ which cannot back-diffuse to the reaction side. Thus the chemical equilibrium on the reaction side is effectively "pulled" across the membrane and toward the production of uncharged product $\underline{C}$. Thereafter, the peptide $\underline{D}$ is converted to aspartame by acid hydrolysis, which removes the formyl and benzyl protecting groups, followed by C-terminal esterification with methanol.

Figure 2:
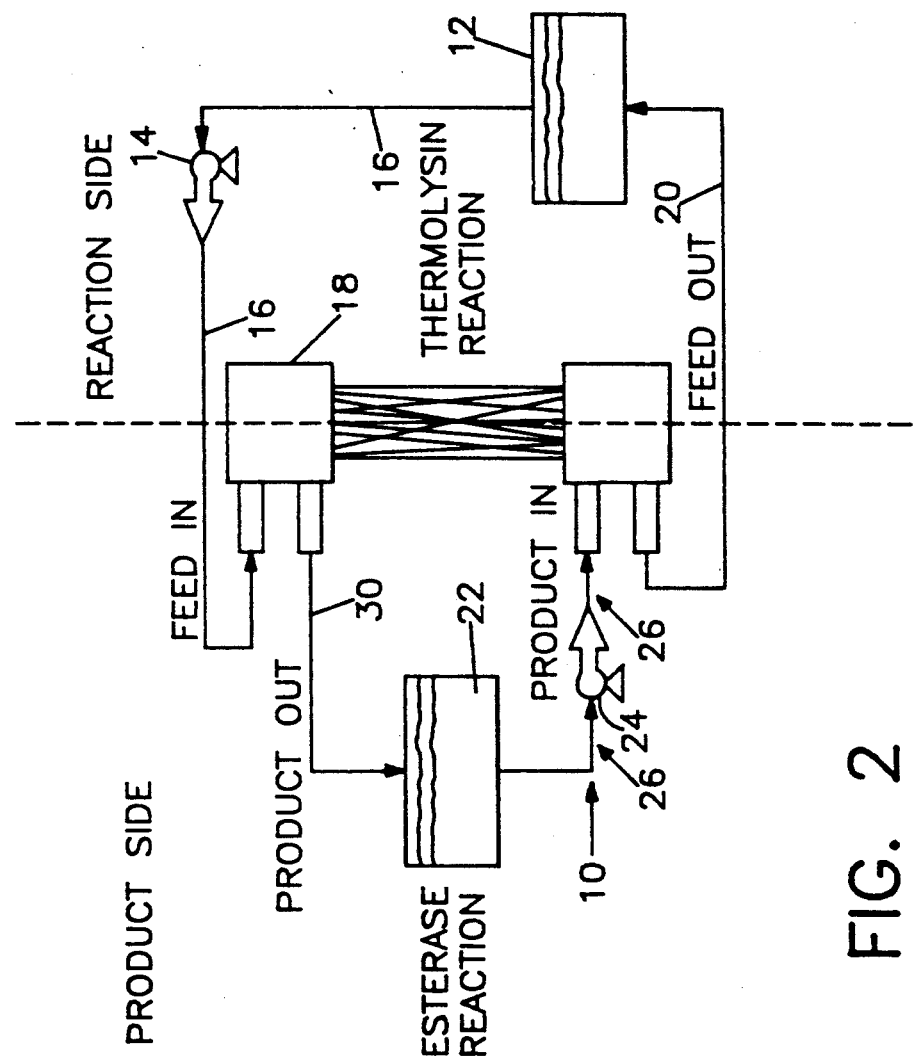
FIG. 2 is a schematic representation of an apparatus for practicing the process of the present invention.

The foregoing method may be practiced in a countercurrent flow membrane reactor/separator 10, as shown in FIG. 2, operating under controlled conditions of pH and temperature, so that a reaction mixture comprising a N-acyl-β-substituted-L-aspartic acid, e.g., N-formyl-β-benzyl-L-aspartate, having a free α-carboxylate group (electronegative species) which is allowed to condense with a reactant, e.g., D, L-phenylalanine methyl ester, having a protonated free α-amino group (electropositive species), under the catalytic action of acidic or neutral proteases active in the pH range of about 4.0–8.0, to yield a fully protected L-aspartyl-L-phenylalanine dipeptide bearing no ionized groups (electroneutral species). On the reaction side of the membrane the reaction mixture is circulated from reactor tank 12 aided by pump 14, through feed-in conduit 16 through separator 18 to feed-out conduit 20 which returns to reactor tank 12. On the product side of the membrane a product mixture or sweep including fully protected uncharged peptide, e.g., N-formyl-β-benzyl-L-aspartyl-L-phenylalanine methyl ester transported across the membrane, is circulated from product reactor tank 22, aided by pump 24, through product sweep in-conduit 26, through the product side of separator 18, to product sweep out-conduit 30. This product mixture includes a second enzyme $E^2$ an esterase, or other suitable reagent, that can cleave at least one of the protected groups borne by the uncharged peptide, thus generating an electrocharged species that cannot escape the sweep stream by back-diffusing through the membrane.

The charged product may be periodically discharged and/or continuously removed from the product phase by conventional means such as ion exchange resins, and the remaining effluent may be recycled through the system. The resulting product bound to the ion-exchange resin may be desorbed and recovered using conventional procedures.

The selection of appropriate deprotection reagent(s) is determined by the chemical nature of the protecting groups used on the reactants, such as, N-protected-L-aspartic acid, and as indicated above the choice of protecting groups is in turn dictated by structural constraints imposed by the active site of the condensing enzyme.

In general, the enzymes useful in the practice of the present invention are proteolytic enzymes, sometimes called proteases, which may be divided into two groups. The more commonly used are endopeptidases, which only cleave inner linkages, and exopeptidases, which only cleave terminal linkages. Useful enzymes include serine proteinases, (EC 3.4.21) such as chymotrypsin, trypsin, subtilisin BNP' and Achromobacter protease; thiol proteinases (EC 3.4.23), such as, papain; carboxyl proteinases (EC 3.4.23), such as, pepsin; and metalloproteinases (EC 3.4.24), such as, thermolysin, prolisin, Tacynasen N (*St. caespitosus*) and Dispase. Binding of the enzymes to insoluble supports, following procedures well known to practitioners of the art, may be incorporated to the practice of this invention; and although binding the enzymes is not an essential step, it may be desirable in certain applications. Among the many proteases potentially useful for the practice of this invention, thermolysin [E.C. 3.4.24] is the condensing enzyme most preferred because of its remarkable thermostability, wide availability, low cost and broad useful pH range between about 5.0 to 9.0. Other preferred proteases include pepsin and penicillopepsin [T. Hofmann and, R. Shaw, *Biochim. Biophys. Acta.* 92 543 (1964)] and, the thermostable protease from Penicillium duponti [S. Emi, D. V. Myers and G.A. Iacobucci, *Biochemistry* 15, 842 (1976)]. They would be expected to function at about pH 5.5, exhibit good stability at such pHs, and do not require the presence of $Zn^{++}$ and $Ca^{++}$ ions to maintain their activity.

The practical realization of enantiomeric selectivity that is, in the case described above, production of only the L,L isomer of the peptide C, is directly related to the enzyme selected, optimal functioning of the membrane, chemical nature of the support material and pH of the aqueous reaction phase.

The preferred membrane for practicing the above-described specific method is a microporous polypropylene support material including a mixture of n-hexadecanol and n-dodecane immobilized therein. This membrane is available from Bend Research, Inc., 64550 Research Road, Bend, Oreg. 97701, U.S.A. under the tradename/designation "Type 1 Hollow Fiber Selective Dialysis Membrane". When operated at pHs of about 5.5, these membranes exhibit a high selectivity, for example, when practicing the process of FIG. 1, selectivity in the range of about 500:1 (W/W) in favor of the uncharged peptide species have been measured. That is, 500 milligrams of the uncharged peptide (C) are transported across the membrane for each milligram of charged reactant ($A^+$ or $E^-$) transported.

As mentioned above, for the application of the present invention it will be necessary, or desirable, to block or protect various functional groups on the reactants and products to prevent undesirable side reactions that could prevent production of the desired product and/or reduce its yield and to suppress electro charges in intermediate peptide. Table I below lists a series of selected combinations of protecting groups and deprotection conditions useful in connection with the practice of this invention.

TABLE I

PROTECTING GROUPS AND DEPROTECTION REAGENTS USEFUL IN THE SYNTHESIS OF ASPARTAME (APM).

| $R^1$ | $R^2$ | $R^3$ | Group Removed/Reagent | Product |
|---|---|---|---|---|
| ØCH₂O— | ØCH₂OCO— | CH₃O— | $R^1,R^2/(Pd)H_2$ | APM |
| ØCH₂O— | —CH=O | CH₃O— | $R^2/H_3O^+$ | β-benzyl-APM |
| ØCH₂O— | —CH=O | CH₃O— | $R^3$/Fungal esterase | N-formyl-β-benzyl-L-aspartyl-L-phenylalanine |
| ter-BuO | —CH=O | CH₃O— | $R^1,R^2/H_3O^+$ | APM |
| CH₃O— | —CH=O | CH₃O— | $R^3$/fungal esterase | N-formyl-isoAPM |
| CH₃O— | —CH=O | CH₃O— | $R^3$/α-chymotrypsin | N-formyl-isoAPM |
| NH₂— | ØCH₂OCO— | CH₃O— | $R^1$/asparaginase | N-CBZ-APM |
|  | L-dihydroorotyl-L-phenylalanine methyl ester |  | $R^1,R^2$/hydantoinase | APM |

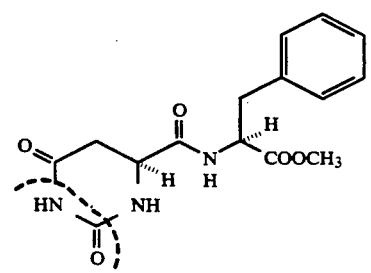

| | | | | |
|---|---|---|---|---|
| CH₃O— | ØCH₂OCO— | CH₃O— | $R^3$/fungal esterase | N-CBZ-iso APM |

TABLE I-continued
PROTECTING GROUPS AND DEPROTECTION REAGENTS USEFUL IN THE SYNTHESIS OF ASPARTAME (APM).

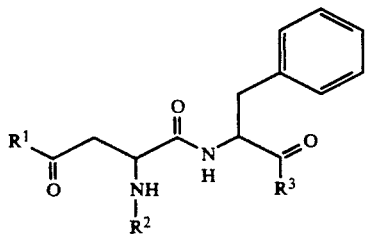

| $R^1$ | $R^2$ | $R^3$ | Group Removed/Reagent | Product |
|---|---|---|---|---|
| $CH_3O-$ | $\phi CH_2CO-$ | $CH_3O-$ | $R^2$/penicillin acylase | APM-$\beta$-methylester |

As a result of the enantioselectivity of selected condensation enzymes and the functional discrimination exerted by the membrane, the practice of the invention using N-formyl-L-aspartyl-$\beta$-benzyl ester and D, L-phenylalanine methyl ester could achieve a 99.8% enantiomeric resolution of the racemic phenylalanine methyl ester reactant, the L-enantiomer appearing as N-formyl-L-aspartyl($\beta$-benzyl)-L-phenylalanine methyl ester, an aspartame derivative, with the unreacted D-enantiomer remaining in the reaction phase.

The D-phenylalanine methyl ester remaining in the reaction phase may be recovered therefrom, re-racemized to the D,L-stage, and recycled into the feedstock. This is an advantage common to many processes employing racemic amino acid reactants, e.g., the '311 process described above.

The economic advantages of the present invention derive, at least in part, from the use of a racemate feed reactant rather than a more expensive pre-resolved L-enantiomer. This advantage is made possible by the in situ optical resolution of the D,L-phenylalanine methyl ester due to: (a) the enantioselectivity of the condensing enzyme; and (b) the high selectivity of the membrane in favor of the uncharged species.

Preferred methods for the low-cost synthesis of racemic phenylalanine are those based on the utilization of benzaldehyde via 5-benzalhydantoin sometimes called the Grace process, or the catalytic carbonylation of benzyl chloride to phenylpyruvic acid a procedure developed by Toyo Soda.

It will be appreciated by those skilled in the art that the practice of this invention is not necessarily restricted to the synthesis of peptide sweeteners, such as aspartame or its analogs and derivatives. The invention may also be used for the synthesis of other useful peptides, di-, tri-, tetra- and pentapeptides, or peptides of higher complexity, that are capable of diffusing through a permselective membrane at a reasonable rate. For example, considering the bond specificity of thermolysin, and assuming the presence of only one thermolysin sensitive bond in the product (indicated by the arrow in the formula below), one could synthesize met-enkephalin (1) by following scheme:

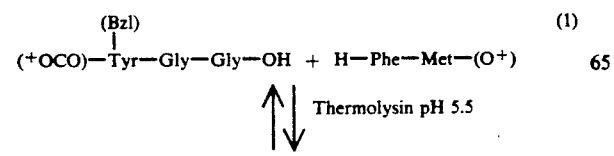

(1)

-continued

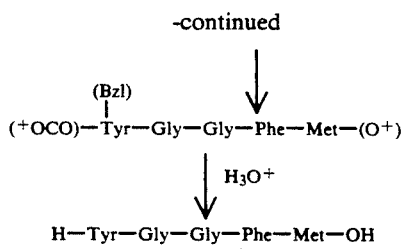

The feasibility of a stepwise total enzymatic synthesis of met-enkephalin using $\alpha$-chymotrypsin and papain has been documented in the literature. See: W. Kullmann, *J. Biol. Chem* 255, 8234 (1980).

Another potentially useful application of the present invention is in the enzymatic synthesis of Gramicidin S (2) by the following scheme:

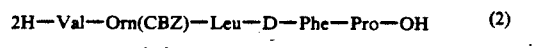

2H—Val—Orn(CBZ)—Leu—D—Phe—Pro—OH    (2)

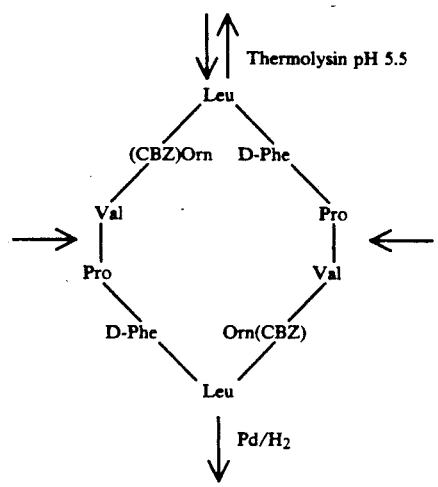

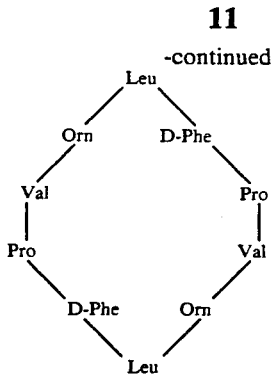

Various other examples of the enzymatic synthesis of useful peptide products where the present invention may find application and described in the literature are the synthesis of angiotensin, substance P, eledoisin, caerulein and Leu-enkephalin.

Those skilled in the art will appreciate that the present invention may also find application to other systems besides peptides.

For example, the use of ester hydrolases like pig liver esterase [EC 3.1.1.1] for the asymmetric resolution of prochiral dicarboxylic acid diesters into chiral monoesters is well known [C. J. Sih et al., *Ann. N. Y. Acad. Sci.* 471, 239 (1986)], the text of which is incorporated herein by reference. It is conceivable that the same enzyme could be used in the fashion described in this invention for the resolution of a (R,S)-carboxylic acid, through the selective transport of a chiral ester through the membrane and the retention of the non-reactive enantiomeric acid in the reaction phase.

The following detailed Examples are presented to further illustrate the present invention.

EXAMPLE 1

An aspartame derivative was prepared in accordance with the present invention as follows:

To a solution containing 5.02 g (20 mmoles) N-formly-L-aspartyl-$\beta$-benzylester, 4.31 g (20 mmoles) L-phenylalanine methyl ester in 100 mL in water, adjusted to pH 5.5, was added 500 mg thermolysin enzyme (Daiwa Chem. Co., Osaka, Japan) representing a total of 20,000 proteolytic units.

The resulting clear reaction mixture was incubated for 15 hrs at 40° C., when the presence of insoluble dipeptide N-formyl-$\beta$-benzyl-L-aspartyl-L-phenylalanine methyl ester became apparent. The resulting mixture was then placed in a 200 mL vessel, connected to the reaction side, in this case tube side, of an experimental hollow-fiber separator of a Bend Research, Inc. "Type 1 Hollow Fiber Selective Dialysis Membrane" that provided 1 square foot of membrane area. The product side of the membrane (shell side of the separator) was connected to a source of aqueous (product) mixture (total volume=200 mL) containing 500 mg of the enzyme Acylase I (EC 3.5.1.14) from Aspergillus Sp. (Sigma A 2156), at pH 7.5. This enzyme, usually described as an aminoacylase, was found to function as a C-terminal esterase, on both N-acetyl- and N-formyl-$\beta$-benzyl aspartame.

The reaction and product mixtures were circulated at room temperature through the hollow fiber separator countercurrently at the rate of 600 mL/min, with the assistance of peristaltic pumps. The configuration of this apparatus resembles that illustrated in FIG. 2. Since both reactions (condensation and the ester hydrolysis) are protogenic, the pH in both the reaction and product mixtures drops as the process progresses. Constancy of pH, in both the reaction and product mixtures, was maintained through the use of pH stats.

The formation of N-formyl-$\alpha$-benzyl-L-aspartyl-L-phenylalanie was monitored by HPLC. Chromatographic analysis was conducted on a Tracor Model 995 instrument along with a LDC Spectromonitor II detector set at 254 nm for the detection of the amino acids, fully protected product dipeptide, and dipeptide. The column used was a NOVA-PAK $C_{18}$ Radial-Pak cartridge, 8 mm×10 cm, housed in a Millipore Waters RCM-100 Radial Compression Module.

The mobile phase used for the detection of the fully protected dipeptide was a v/v mixture of 45% methanol (HPLC grade) 5% tetrahydrofuran (HPLC grade); and 50% of a 1% $KH_2PO_4$ buffer solution. For the detection of the product dipeptide, the mobile phase consisted of a v/v mixture of 40% methanol and 60% of a 1% $KH_2PO_4$ buffer solution (1 mL of triethylamine per liter solvent was added to minimize tailing and the pH was adjusted down to 4.3 using 80% phosphoric acid). The flow rate was kept at 1 mL/minute.

The HPLC data relating to formation of N-formyl-$\alpha$-benzyl-L-aspartyl-L-phenylalanine is summarized in Table II below, and is expressed as the total amount (mg) of product dipeptide accumulated in the product solution as a function of time.

The valve of the uncharged dipeptide concentration at equilibrium which corresponds to its saturation point in water at pH 5.5, was found to be about 0.05% at 25° C. The amount of uncharged dipeptide transported per square foot of membrane per hour was found to be about 200 mg, indicating that maintenance of the equilibrium required dissolution of insoluble dipeptide and/or dipeptide synthesis de novo. Almost complete dissolution of the insoluble uncharged phase dipeptide in the reaction mixture was observed after about 5 hrs, when the reaction was stopped. A plot of the data of Table II is shown in FIG. 3. The linear function indicates that the transfer of peptide across the membrane proceeds at a steady state. The observed rate of formation of product dipeptide of about 200 mg./ft²/hr (Table II) was confirmed similar to the flux of uncharged dipeptide across the membrane (190 mg./ft²/hr) measured at 0.05% in water as was anticipated on theoretical grounds.

At this point the described system would be expected to continue in steady state if continuous addition were made to the reaction mixture of the two amino acid reactants, at a rate of about 120 mg/hr each, to keep the system saturated in uncharged dipeptide.

In order to fully realize the membrane's selectivity the intercalation of a second membrane in series with the first membrane before the contact with the second enzyme may be necessary because the selectivity across a single membrane is lower due to the high amino acid concentration in the reaction solution.

The product solution (200 mL) was recovered, adjusted to pH 2.5 and cooled at 4° C. overnight. The precipitate collected was recovered and recrystallized from MeOH:$H_2O$ to give 307 mg of N-formyl-$\beta$-benzyl-L-aspartyl-L-phenylalanine $[\alpha]_D^{25°} = -5.6°$ (C=1.2; EtOH), identical (IR, 13C-NMR) to an authentic sample prepared by the batch hydrolysis of N-formyl-$\beta$-benzyl-aspartame with Aspergillus esterase, $[\alpha]_D^{25°} = -5.3°$ (C=1.3; EtOH).

TABLE II

| Time (min) | Amount peptide/product solution (mg) |
| --- | --- |
| 30 | 124 |
| 60 | 228 |
| 120 | 412 |
| 180 | 617 |
| 240 | 882 |
| 300/ | 1015 |

EXAMPLE 2

An experiment similar to that of Example 1 was conducted, except for the use of 8.63 g D, L-phenylalanine methyl ester instead of the L-enantiomer. The results are summarized in Table III. Isolation of the uncharged peptide from the 200 mL of product solution gave 310 mg of product, $[\alpha]_D^{25°} = -6.4°$ (C=1.4; EtOH), identical in all respects (IR, 13C-NMR) to an authentic sample of N-formyl-$\beta$-benzyl-L-aspartyl-L-phenylalanine.

TABLE III

| Time (min) | Amount peptide/product solution (mg) |
| --- | --- |
| 30 | 166 |
| 60 | 258 |
| 120 | 475 |
| 180 | 686 |
| 240 | 996 |
| 300 | 1073· |

A plot of the data summarized in Table III (FIG. 3) again showed the existence of a steady state process when the reactor was operated with D,L-phenylalanine methyl ester. The stereospecificity of thermolysin is demonstrated by the exclusive formation of the same L,L-dipeptide described in Example 1. The D-phenylalanine methyl ester retained in the tube phase (reaction mixture) did not inhibit the overall kinetics of peptide formation.

EXAMPLE 3

A mixture of 1.0 g N-formyl-$\beta$-benzyl-L-aspartyl-L-phenylalanine methyl ester, prepared in accordance with Example 1, 4.0 mL water, 4.0 mL tetrahydrofuran, and 1.0 mL conc. hydrochloric acid (12N) was heated at reflux for 9 hrs. The mixture was then cooled and the pH adjusted to 4.0 with 50% NaOH solution. The tetrahydrofuran was then removed by evaporation at <35° and 20 mm Hg. Crystallization was completed by storage at 5° C. for 1 hr, the sample then filtered, washed with 1 mL ice water, and dried in vacuo to give 367 mg of white solid. This material was identical to an authentic sample of aspartyl phenylalanine by HPLC and IR comparison. $[\alpha]_D^{25°} = +12°$ (C=0.5; 0.1N HCl in 50% MeOH).

Aspartylphenylalanine has been converted to aspartame by treatment with methanol and hydrochloric acid, as described in G. L. Bachman and B. D. Vineyard, U.S. Pat. No. 4,173,562, example #1.

EXAMPLE 4

An experiment similar to that of Example 1 was conducted, except for the use 5.65 g (20.1 mmoles) N-carbobenzoxy-L-aspartic acid $\beta$-methyl ester and 4.38 g (20.3 mmoles) L-phenylalanine methyl ester as reactants. The amino acids were dissolved in 100 mL water, the pH of the solution adjusted to 5.5, and 500 mg of thermolysin Daiwa (20,000 proteolytic units) was added. The solution was preincubated for 15 hours at 40° C., when a substantial amount of N-CBZ-($\beta$-methyl ester)-L-asp-L-phenylalanine methyl ester was precipitated. The suspension was connected to the tube side of a "Type 1 Hollow Fiber Selective Dialysis Membrane" (Bend Research Inc.) containing 1 ft² of membrane surface, and the machine was operated at room temperature for 5 hours against a shell side phase of 200 mL water containing 500 mg Acylase I (Sigma) at pH 7.5. The accumulation of peptide product in shell phase was monitored by HPLC, and the results are reproduced in Table IV and FIG. 4.

After 5 hours run the reaction was stopped, the shell side phase (200 mL) was recovered, adjusted to pH 2.5 and stored overnight at 4° C. The product precipitated was collected and recrystallized from CH$_3$OH:H$_2$O to yield 405 mg (86% recovery) of N-CBZ-($\beta$-methyl ester)-L-asp-L-phenylalanine (N-CBZ-iso-APM) $[\alpha]_D^{25°} = +6.0°$ (C=1.1, EtOH), identical (¹³C-NMR) to an authentic sample of N-CBZ-iso-APM, $[\alpha]_D^{25°} = +5.5°$ (C=1.1, EtOH), prepared by chemical coupling and partial esterolysis with Acylase I.

TABLE IV

| Time (min) | Amount peptide/product solution (mg) |
| --- | --- |
| 30 | 177 |
| 60 | 214 |
| 120 | 333 |
| 180 | 381 |
| 240 | 459 |
| 300 | 470 |

As observed before in the experiments of Examples 1 and 2, the plot of FIG. 4 indicates that the accumulation of N-CBZ-iso-APM proceeded at a steady rate of about 200 mg/hr.

The conversion of N-CBZ-iso-APM to APM can be practiced under the conditions described in Example 3.

What is claimed is:

1. A method for the enzymatic synthesis of peptides, comprising the steps of:
   condensing a N-acyl-$\beta$-substituted-L-aspartic acid having an $\alpha$-carboxylate group with a phenylalanine lower alkyl ester having an $\alpha$-ammonium group, in an aqueous reaction mixture including a condensation enzyme to form N-acyl-L-aspartyl-($\beta$-substituted)-L-phenylalanine lower alkyl ester) an uncharged peptide; and
   transporting the uncharged peptide from the aqueous reaction mixture across an ion rejection membrane into a product mixture.

2. The method recited in claim 1 wherein the condensation enzyme is a peptide forming acidic or neutral protease active in a pH range of about 4.0 to 8.0.

3. The method recited in claim 1 wherein the condensation enzyme is a protease selected from the group consisting of serine proteinases, thiol proteinases, carboxyl proteinases and metalloproteinases.

4. The method recited in claim 1 wherein the condensation enzyme is selected from the group consisting of chymotrypsin, trypsin, substilisin BNP' Achromobacter protease, papain, pepsin, thermolysin and prolisin; and the pH of the reaction mixture is between about 4.0 to 8.0.

5. The method recited in claim 1 wherein the condensation enzyme is thermoylsin and the pH of the reaction mixture is about 5.5.

6. The method recited om claim 4 wherein the membrane comprises a water-immiscible organic liquid immobilized by capillarity in pores in a microporous sheet the organic liquid being a solvent for the uncharged peptide.

7. The method recited in claim 6 wherein the microporous sheet is made from a material selected from a group consisting of polytetrafluoroethylene and polypropylene and the solvent comprises at least one compound selected from a group consisting of n-1-decanol, n-hexadecanol, n-dodecanol and mixtures thereof.

8. The method recited in claim 6 wherein the membrane is a Bend, Type 1 Hollow Fiber Selective Dialysis Membrane.

9. The method recited in claim 3 wherein the pH of the aqueous solution is between about 4.0 and 6.0.

10. The method recited in claim 4 wherein the pH of the aqueous solution is between about pH 4.0 and 6.0.

11. The method recited in claim 5 wherein the first compound is D,L-phenylalanine methyl ester, and the second compound is N-acyl-$\beta$-substituted-L-aspartic acid having an $\alpha$-carboxylate group.

12. The process recited in claim 11 wherein the N-acyl group is selected from the group consisting of $\phi CH_2OCO-$, $-CH=O$ and $\phi CH_2CO-$; and the $\beta$-substituent is selected form the group consisting of $\phi CH_2O-$, ter BuO—, $CH_3-NH_2-$.

13. A method for the enzymatic synthesis of peptides comprising th steps of:
condensing first and second amino acid compounds in an aqueous initial reaction mixture to form an uncharged compound;
transporting the uncharged compound into an aqueous second reaction mixture accross a membrane that will not transport substantial amounts of the amino acid compounds; and
converting the transported uncharged compound to a form that cannot be retransported across the membrane to the initial mixture.

* * * * *